(12) United States Patent
Stefanovic

(10) Patent No.: US 11,554,121 B2
(45) Date of Patent: Jan. 17, 2023

(54) COMPOSITIONS AND METHODS FOR INHIBITING TYPE 1 COLLAGEN PRODUCTION

(71) Applicant: Florida State University Research Foundation, Inc., Tallahassee, FL (US)

(72) Inventor: Branko Stefanovic, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 31 days.

(21) Appl. No.: 17/217,091

(22) Filed: Mar. 30, 2021

(65) Prior Publication Data

US 2021/0299136 A1 Sep. 30, 2021

Related U.S. Application Data

(60) Provisional application No. 63/001,866, filed on Mar. 30, 2020.

(51) Int. Cl.
*A61K 31/542* (2006.01)
*A61P 19/04* (2006.01)

(52) U.S. Cl.
CPC ............ *A61K 31/542* (2013.01); *A61P 19/04* (2018.01)

(58) Field of Classification Search
CPC .............................. A61P 17/02; C07D 403/04
See application file for complete search history.

(56) References Cited

U.S. PATENT DOCUMENTS 8,697,385 B1 * 4/2014 Stefanovic ............... C12Q 1/37
435/23

FOREIGN PATENT DOCUMENTS

WO 2016142902 A1 9/2016

OTHER PUBLICATIONS

Wang et al. ( BioMed Research International, vol. 2015, Article ID 697958, pp. 1-13 ) (Year: 2015).*
Sivakumar et al. (Scientia Pharmaceutica, 2013; 81, pp. 933-950) (Year: 2013).*
International Search Report dated Jun. 10, 2021 for PCT/US221/24820.
Sivakumar et al.; "Isolation and Characterisation of Degradation Impurities in the Cefazolin Sodium Drug Substance"; Sci. Pharm; vol. 81(4); pp. 933-950; 2013.
Wang et al.; "Mass Spectral Profile for Rapid Differentiating Beta-Lactams from Their Ring-Opened Impurities" BioMed Research International; vol. 2015, Article ID 697958; 13 pages.

* cited by examiner

*Primary Examiner* — Savitha M Rao
(74) *Attorney, Agent, or Firm* — Christopher M. Ramsey; GrayRobinson, P.A.

(57) ABSTRACT

This discloses that compounds of Formula 1 may be used as antifibrotics because they inhibit type 1 collagen production. In particular, this discloses a pharmaceutical composition containing one or more compounds of Formula 1 and methods of using compounds of Formula 1 in fibrosis treatment and inhibiting type 1 collagen synthesis.

10 Claims, 17 Drawing Sheets cephalosporin cefdinir cefixime

Formula 1

Formula 2

Formula 3

COMPOSITIONS AND METHODS FOR INHIBITING TYPE 1 COLLAGEN PRODUCTION

CROSS-REFERENCE TO RELATED APPLICATION

This claims the benefit of priority from U.S. Application No. 63/001,866, filed Mar. 30, 2020, which is incorporated by reference in its entirety.

FIELD

This relates to the field of inhibiting type 1 collagen synthesis and, more particularly, to compounds that inhibit collagen synthesis.

BACKGROUND

Collagen is a protein in the body that gives bones, connective tissues, and organs their physical structure. Different forms of collagen are identified by their "types." Type 1 collagen, the primary form found in the human body, is found in the skin, tendons, ligaments, bones, organs, and vascular system and has a fiber-like structure.

If the body produces excessive amounts of type 1 collagen, this can lead to a condition called fibrosis. Fibrosis is the presence of excess connective tissue in a region of the body. Excess connective tissue in an organ can interfere with the organ's functions. There are many diseases related to fibrosis, some of which include arterial hardening, cirrhosis, scleroderma, and myelofibrosis. Fibrosis-related diseases are a major medical problem throughout the world.

BRIEF SUMMARY

It has now been discovered that cephalosporin-related compounds that are sometimes found as impurities in commercial cephalosporin antibiotic preparations have antifibrotic activity.

An example of an antifibrotic composition includes a pharmaceutical dosage form that is substantially cephalosporin free and includes a compound of formula

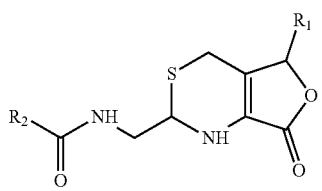

wherein where R1 and R2 are, independently, at least one member selected from the group consisting of H, alkyl, alkenyl, alkynyl, aryl, hydroxy, carboxy, acyl, nitro, phosphor, halo, sulfo, ester, ether, and amino; or a pharmaceutically acceptable salt thereof. Optional features of the composition may include one or more of the following features.

Substantially cephalosporin free may be 0%-5% w/w cephalosporin in the pharmaceutical dosage form.

Some examples of the pharmaceutical dosage form may have no substantial antibacterial efficacy.

R2 may be selected from

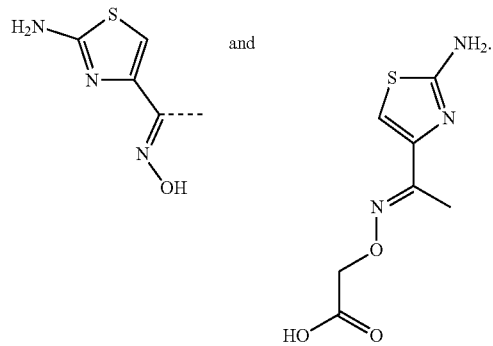

The formula may be

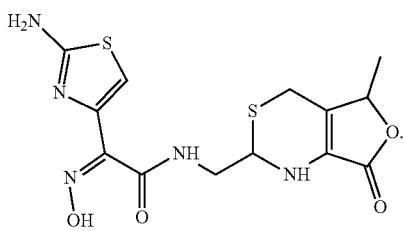 [SMILES: CC1OC(=O)C2=C1CSC(CNC(=O)/C(=N\O)c1csc(N)n1)N2]

The formula may be

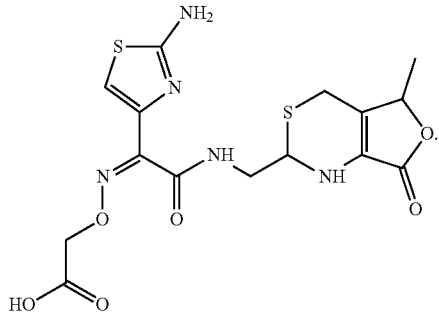 [SMILES: CC1OC(=O)C2=C1CSC(CNC(=O)/C(=N\OCC(=O)O)c1csc(N)n1)N2]

An example of a treatment method includes administering to a patient having a fibrotic condition a therapeutically effective amount of the composition to a patient. Optional features of this method may include one or more of the following features.

Substantially cephalosporin free may be 0%-5% w/w cephalosporin in the pharmaceutical dosage form.

Some examples of the pharmaceutical dosage form may have no substantial antibacterial efficacy.

R2 may be selected from

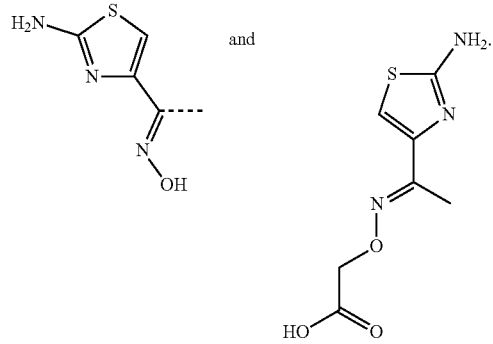

The formula may be

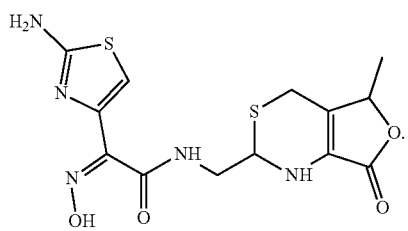 [SMILES: CC1OC(=O)C2=C1CSC(CNC(=O)/C(=N\O)c1csc(N)n1)N2]

The formula may be

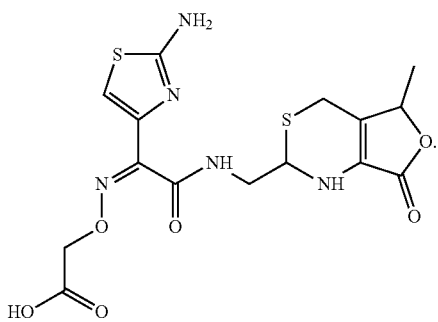 [SMILES: CC1OC(=O)C2=C1CSC(CNC(=O)/C(=N\OCC(=O)O)c1csc(N)n1)N2]

The fibrotic condition may be at least one of a pulmonary fibrosis, a liver fibrosis, a heart fibrosis, a brain fibrosis, a circulatory system fibrosis, a skin fibrosis, and an intestinal fibrosis.

Administering may be by oral administration and/or administration by injection.

An example of a method of inhibiting type 1 collagen synthesis includes contacting at least one cell expressing type 1 collagen with the composition.

The cell may be at least one cell selected from a lung cell, a liver cell, a heart cell, a brain cell, a circulatory system cell, a skin cell, and an intestinal cell. Optional features of this method include one or more of the following features.

Substantially cephalosporin free may be 0%-5% w/w cephalosporin in the pharmaceutical dosage form.

In certain examples, the pharmaceutical dosage form may have no substantial antibacterial efficacy.

R2 may be selected from

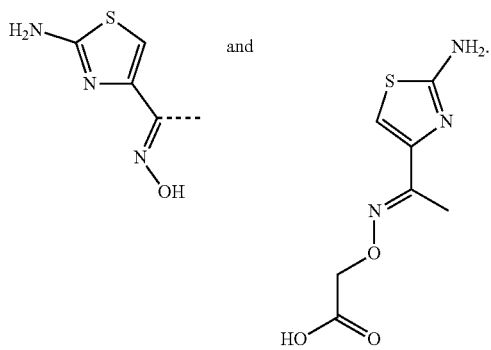

The formula may be

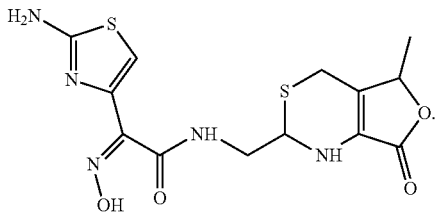 [SMILES: CC1OC(=O)C2=C1CSC(CNC(=O)/C(=N\O)c1csc(N)n1)N2]

The formula may be

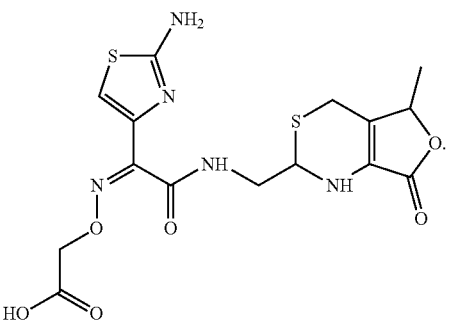 [SMILES: CC1OC(=O)C2=C1CSC(CNC(=O)/C(=N\OCC(=O)O)c1csc(N)n1)N2]

The lower panel is the quantification of expression in three independent experiments.

DETAILED DESCRIPTION OF EXAMPLE EMBODIMENTS

Many cephalosporins fall into a class of antibiotic drugs used to treat a wide range of bacterial infections by inhibiting enzymes in the cell walls of susceptible bacteria.

Figure 1:
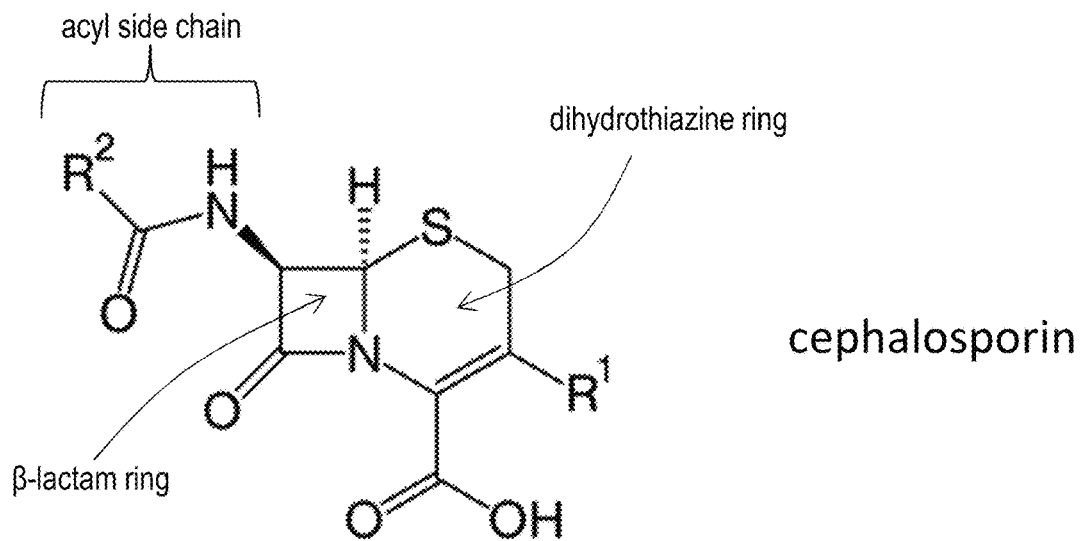
FIG. 1 is the structure of an example of a cephalosporin.
Figure 1:
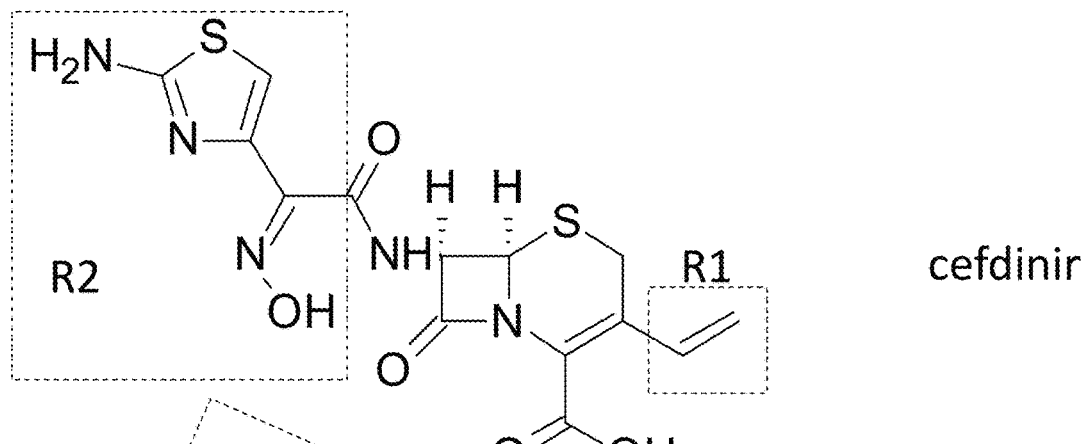
Figure 1:
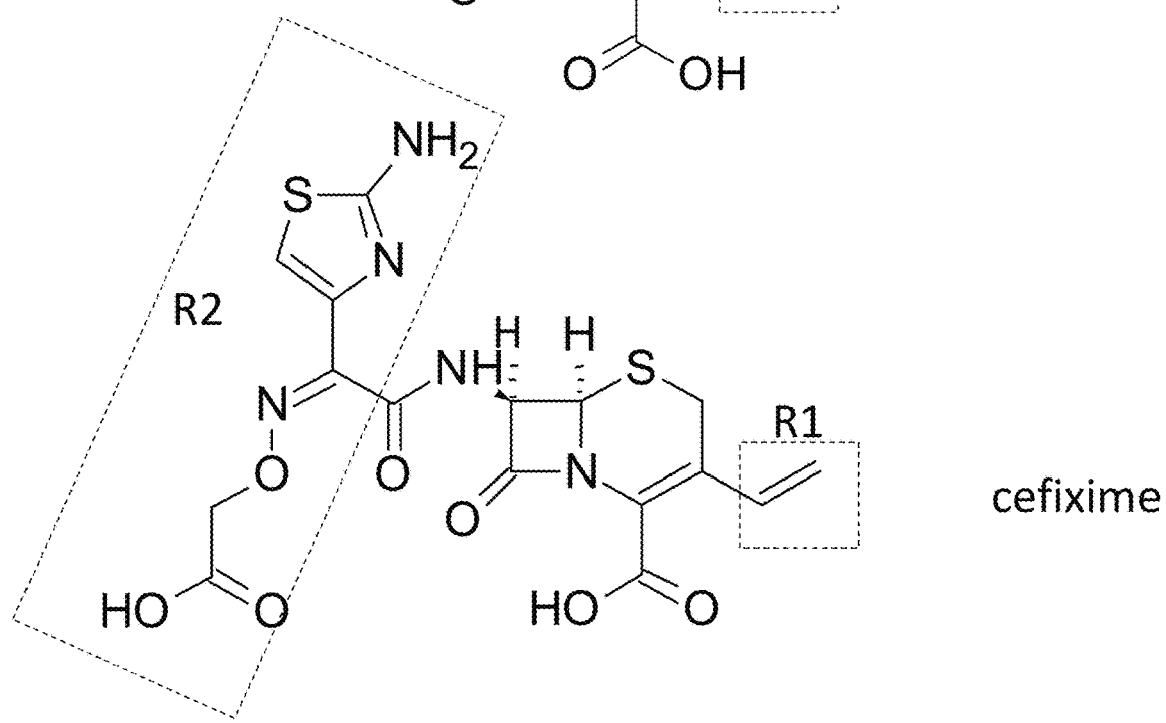

The core structure of a cephalosporin is shown in FIG. 1. It generally includes a dihydrothiazine ring, a β-lactam ring, and an acyl side chain. R1 and R2 refer to "R" groups commonly used by organic chemists to refer to interchangeable moieties. Cefixime and cefdinir, examples of cephalosporins, are provided in FIG. 1 with their R1 and R2 groups indicated.

It has now been discovered that at least some cephalosporin derivatives are effective for inhibiting type 1 collagen synthesis by cells and, therefore, may be used as antifibrotic drugs to treat fibrotic conditions. Those cephalosporin derivatives are effective to decrease the binding affinity of LARP6 for the 5' stem-loop of collagen mRNAs. These compounds differ from their cephalosporin counterparts by excluding the cephalosporin's lactam ring, which is needed for antimicrobial activity of the cephalosporin, but retaining the imine side group.

LARP6 regulates Type I collagen expression in fibrosis, which is characterized by excessive synthesis of type I collagen in various organs. LARP6 binds a unique sequence present in type I collagen mRNAs, the 5' stem-loop (5'SL). This binding regulates translation of type I collagen mRNAs and is necessary for fibrosis development in vivo. Mice in which binding of LARP6 to 5'SL is genetically abolished are resistant to liver fibrosis. This indicates that the inhibitors of LARP6 binding to collagen mRNAs can be specific and effective antifibrotic drugs. U.S. Pat. No. 8,697,385 describes a method of screening a compound for its ability to interfere with collagen synthesis that takes advantage of this property of LARP6. Such a method may be used to screen different cephalosporins for antifibrotic activity.

An example of an antifibrotic compound includes the formula

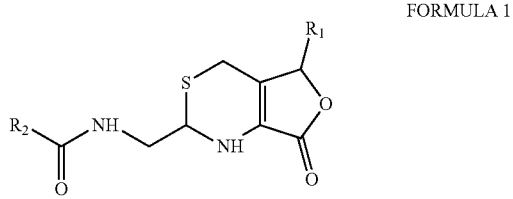

FORMULA 1 or a pharmaceutically acceptable salt thereof.

Certain examples of the compounds of Formula 1 are have substantially no antibacterial efficacy. Antibacterial efficacy may be measured according to standard USP <51> specification for antimicrobial effectiveness testing. A compound may be considered as having substantially no antibacterial efficacy, for example, if it exhibits not more than 2 log reduction from the initial bacteria count at 14 days and no increase from the 14 day count to 28 days using USP <51> procedures. By having substantially no antibacterial efficacy, the compound of Formula 1 may make a safer antifibrotic drug.

The compounds of Formula 1 may have stereoisomers. The compounds may include any isomer of Formula 1 or mixtures of such isomers. Some compounds of Formula 1 have one or more asymmetric carbon atoms and may be obtained as a racemic mixture of stereoisomers which can be resolved.

The compounds of Formula 1 may have tautomers, meaning they may exist as two or more chemical compounds that are capable of interconversion. This often means the exchange of a hydrogen atom between two other atoms. Tautomers exist in equilibrium with each other, thus attempts to prepare the separate forms usually results in the formation of a tautomer mixture.

Some compounds of Formula 1 that are basic may form pharmaceutically acceptable salts with inorganic acids such as hydrohalic acids such as hydrochloric acid and hydrobromic acid, sulphuric acid, nitric acid and phosphoric acid, and the like, and with organic acids such as acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to conventional methods for forming and isolating pharmaceutically acceptable salts.

R1 and R2 may independently be at least one member selected from the group consisting of H, alkyl, alkenyl, alkynyl, aryl, alkoxy, hydroxy, carboxy, acyl, nitro, phosphor, halo, sulfo, ester, ether, and amino.

In certain examples, an alkyl group may be a straight, cyclic, or branched chain alkane hydrocarbon residue containing 1 to 12 carbon atoms. In certain examples, the alkyl group may be a straight or branched chain hydrocarbon residue containing 1 to 7 carbon atoms. Examples of particular alkyl groups include methyl, ethyl, propyl, isopropyl, n-butyl, isobutyl, and tert-butyl. The alkyl group may be substituted with substituents.

In certain examples, an alkenyl group may be a straight, cyclic, or branched chain alkene hydrocarbon residue containing 1 to 12 carbon atoms. In certain examples, the alkenyl group may be a straight or branched chain alkene hydrocarbon residue containing 1 to 7 carbon atoms. Examples of particular alkenyl groups include methenyl, ethenyl, propenyl, isopropenyl, and butenyl. The alkenyl group may be substituted with substituents.

In certain examples, an alkynyl group may be a straight, cyclic, or branched chain alkyne hydrocarbon residue containing 2 to 12 carbon atoms. In certain examples, the alkynyl group may be a straight or branched chain alkyne hydrocarbon residue containing 2 to 7 carbon atoms. Examples of particular alkynyl groups include methynyl, ethynyl, propynyyl, isopropynl, and butenyl. The alkenyl group may be substituted with substituents.

In certain examples, an aryl group may be a substituted phenyl or napthyl. Aryl groups may include examples such as benzyl, tolyl, xylyl, and the like. Suitable substituents for aryl may be, for example, alkyl, halogen, hydroxy, and optionally substituted alkyl, haloalkyl, alkenyl, alkynyl and aryloxy.

In certain examples, an alkoxy group may be optionally substituted straight or branched chain alkyl-oxy group where the alkyl portion is defined above. Examples may include methoxy, ethoxy, n-propyloxy, i-propyloxy, n-butyloxy, i-butyloxy, tert-butyloxy, pentyloxy, hexyloxy, and heptyloxy.

In certain examples an acyl group may be a group containing R—C=O optionally substituted with any of the other groups mentioned herein.

Figure 2:
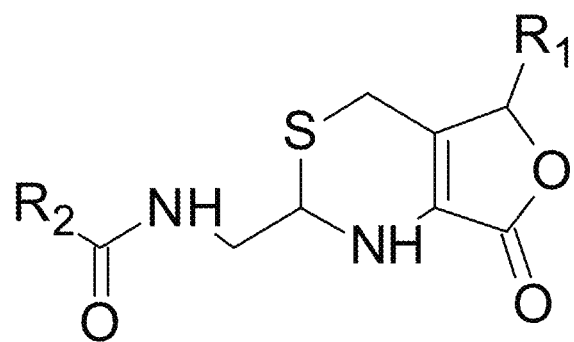
FIG. 2 shows examples of antifibrotic cephalosporin derivatives.
Figure 2:
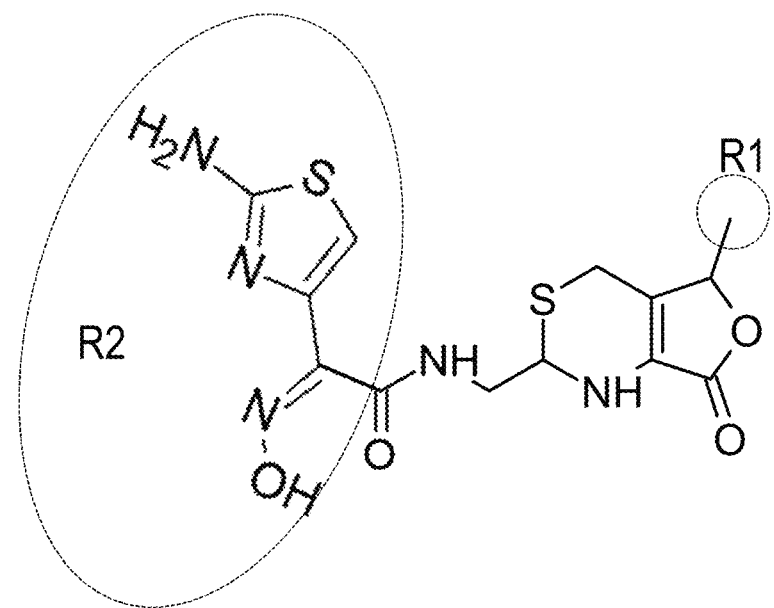
Figure 2:
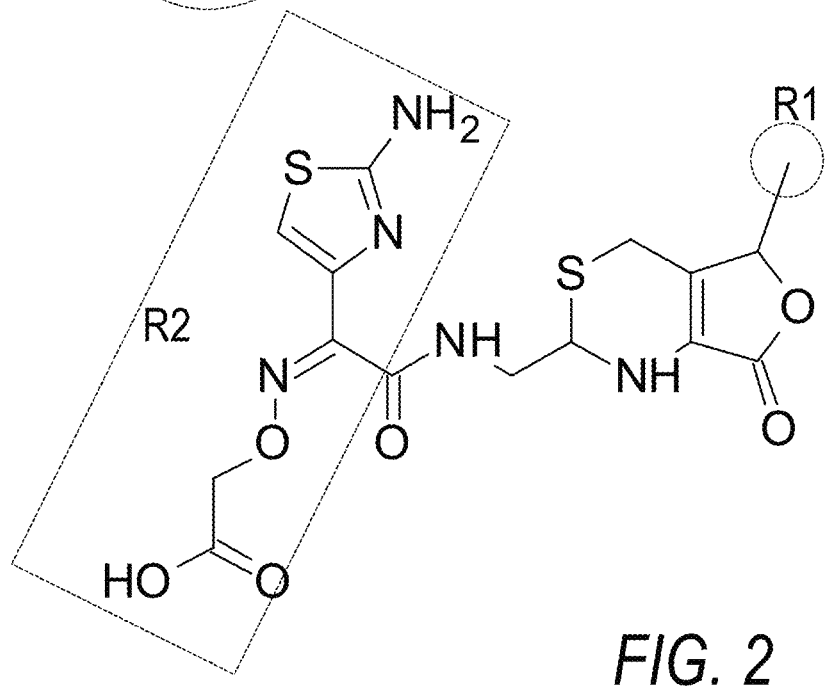
Figure 3A:
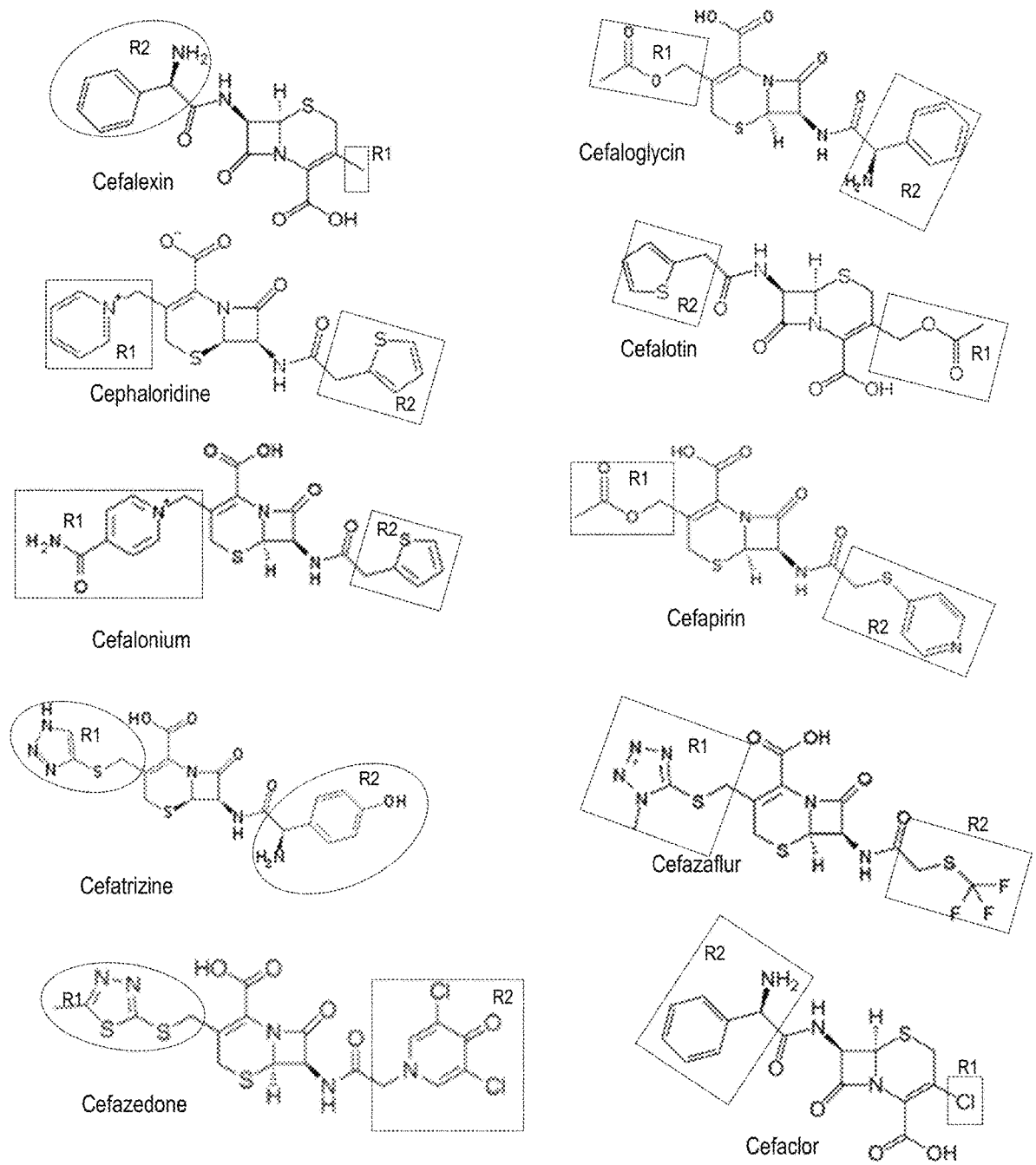
FIG. 3A shows examples of cephalosporins with examples of R1 and R2 groups indicated.
Figure 3B:
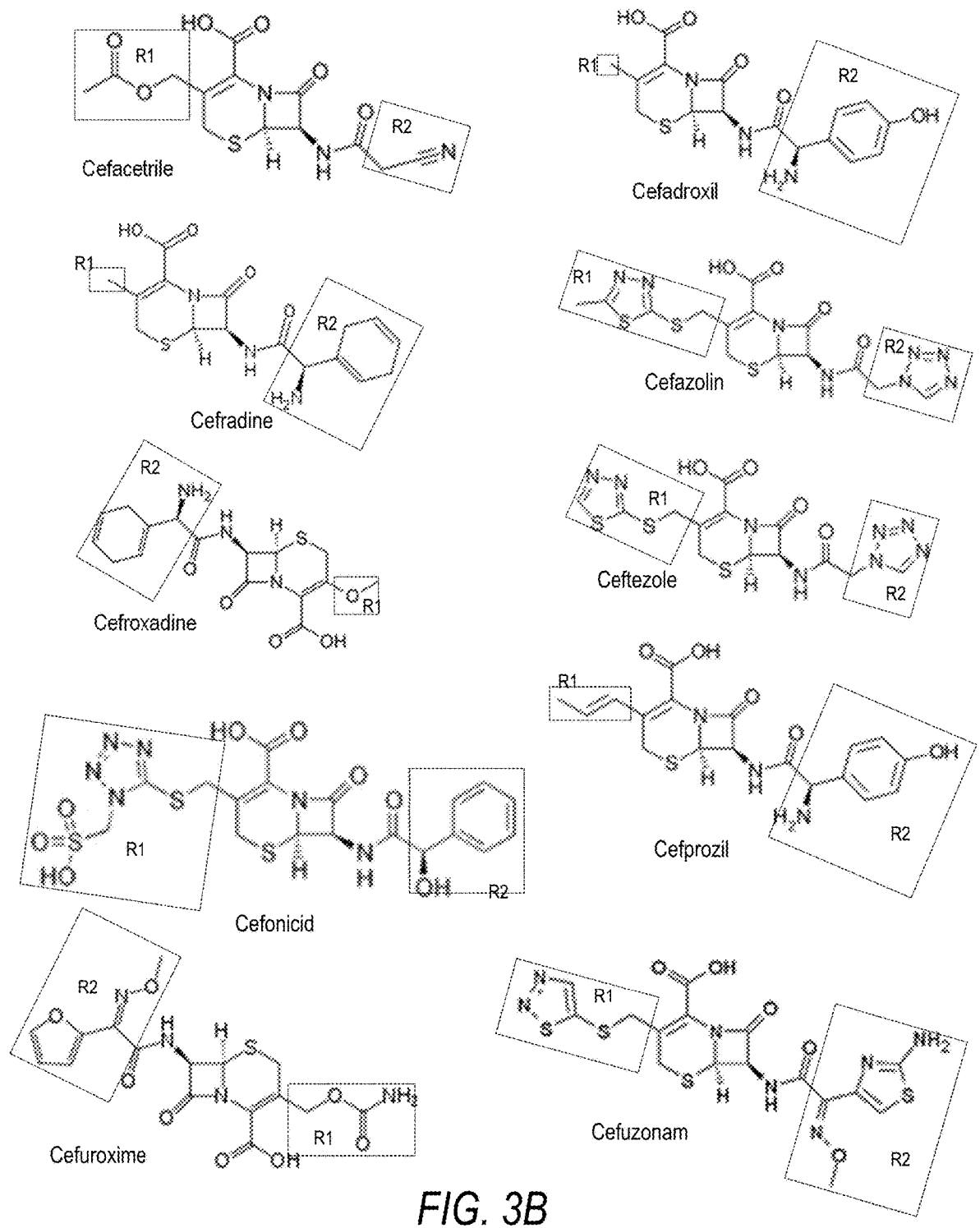
FIG. 3B shows examples of cephalosporins with examples of R1 and R2 groups indicated.
Figure 3C:
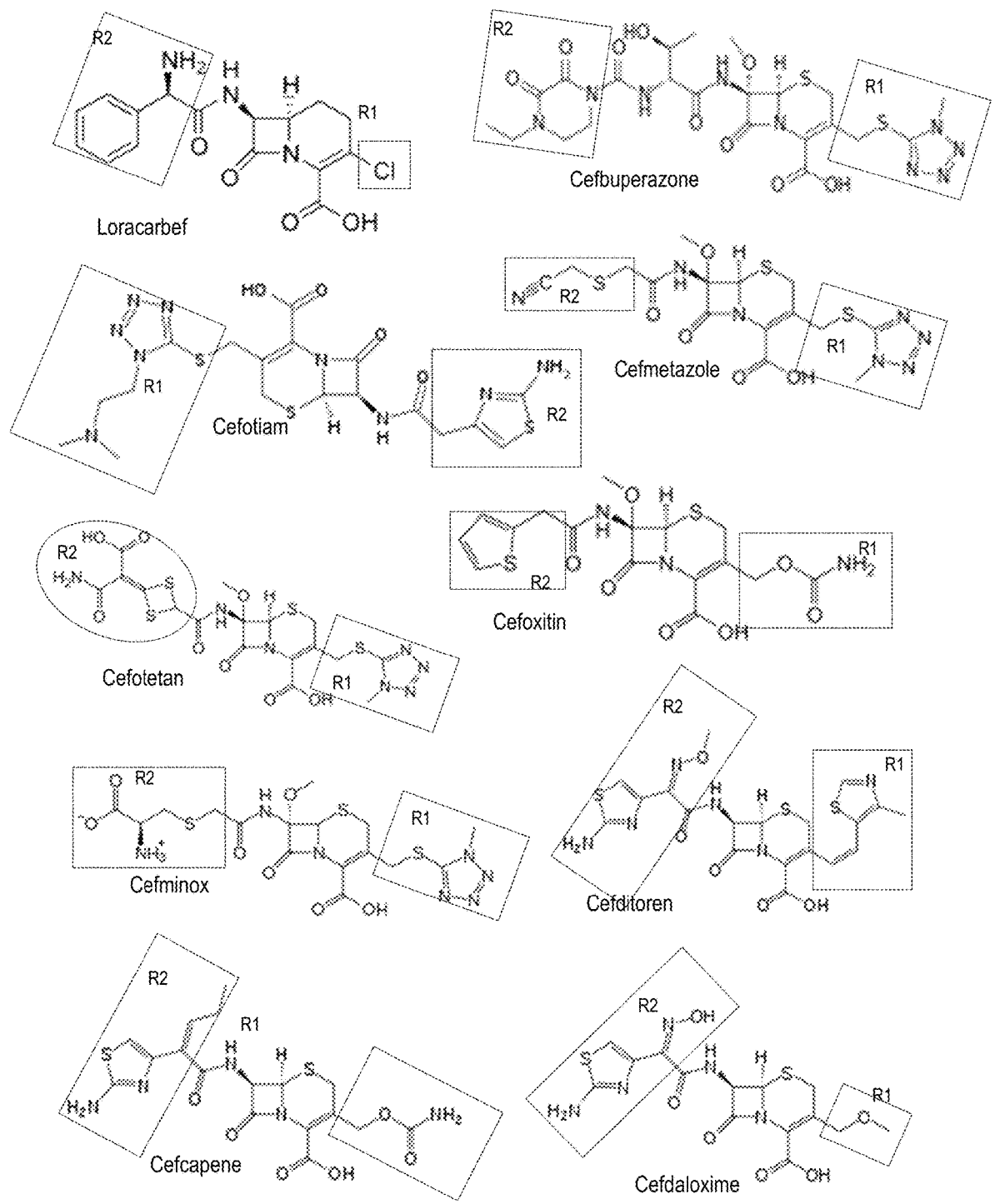
FIG. 3C shows examples of cephalosporins with examples of R1 and R2 groups indicated.
Figure 3D:
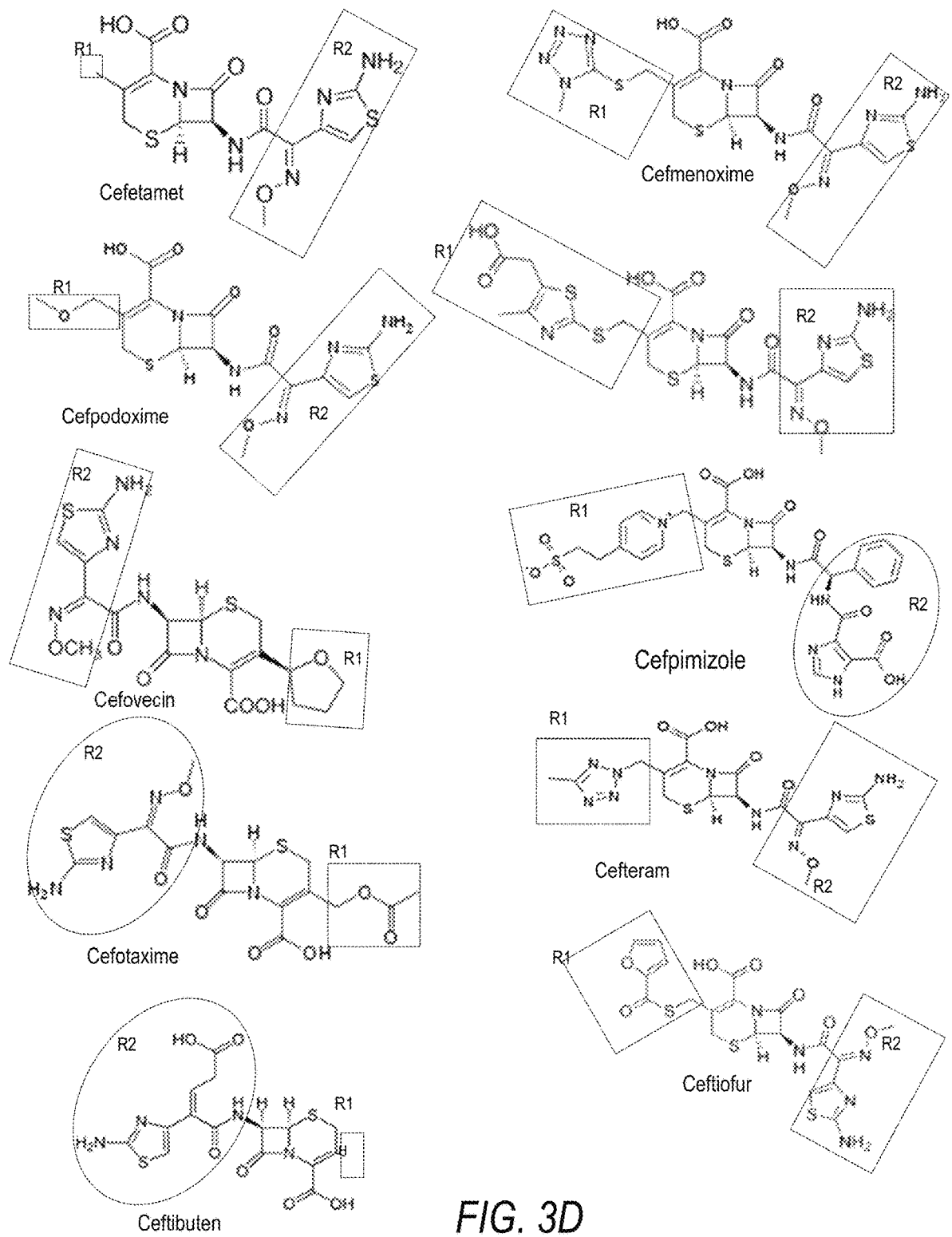
FIG. 3D shows examples of cephalosporins with examples of R1 and R2 groups indicated.
Figure 3E:
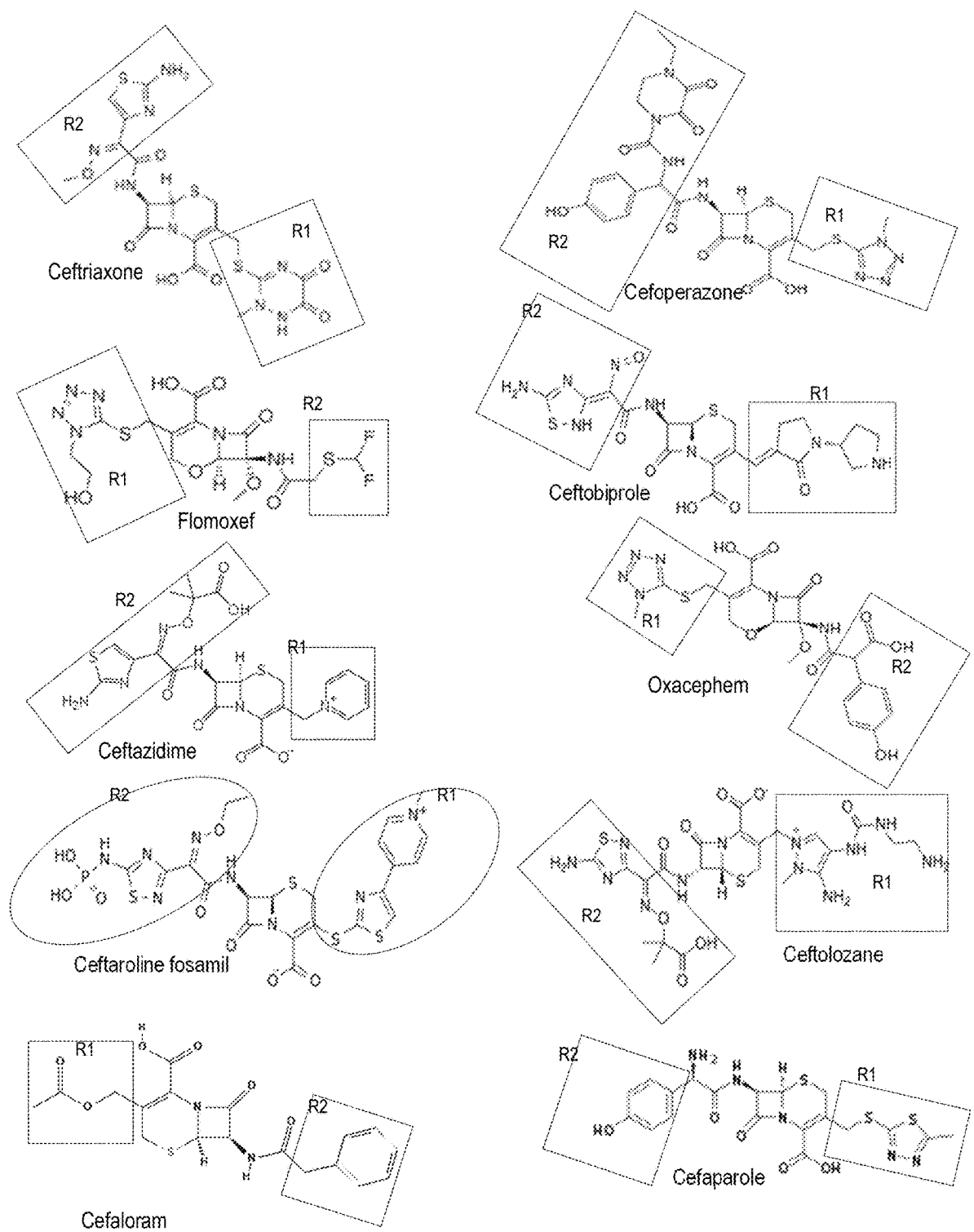
FIG. 3E shows examples of cephalosporins with examples of R1 and R2 groups indicated.
Figure 3F:
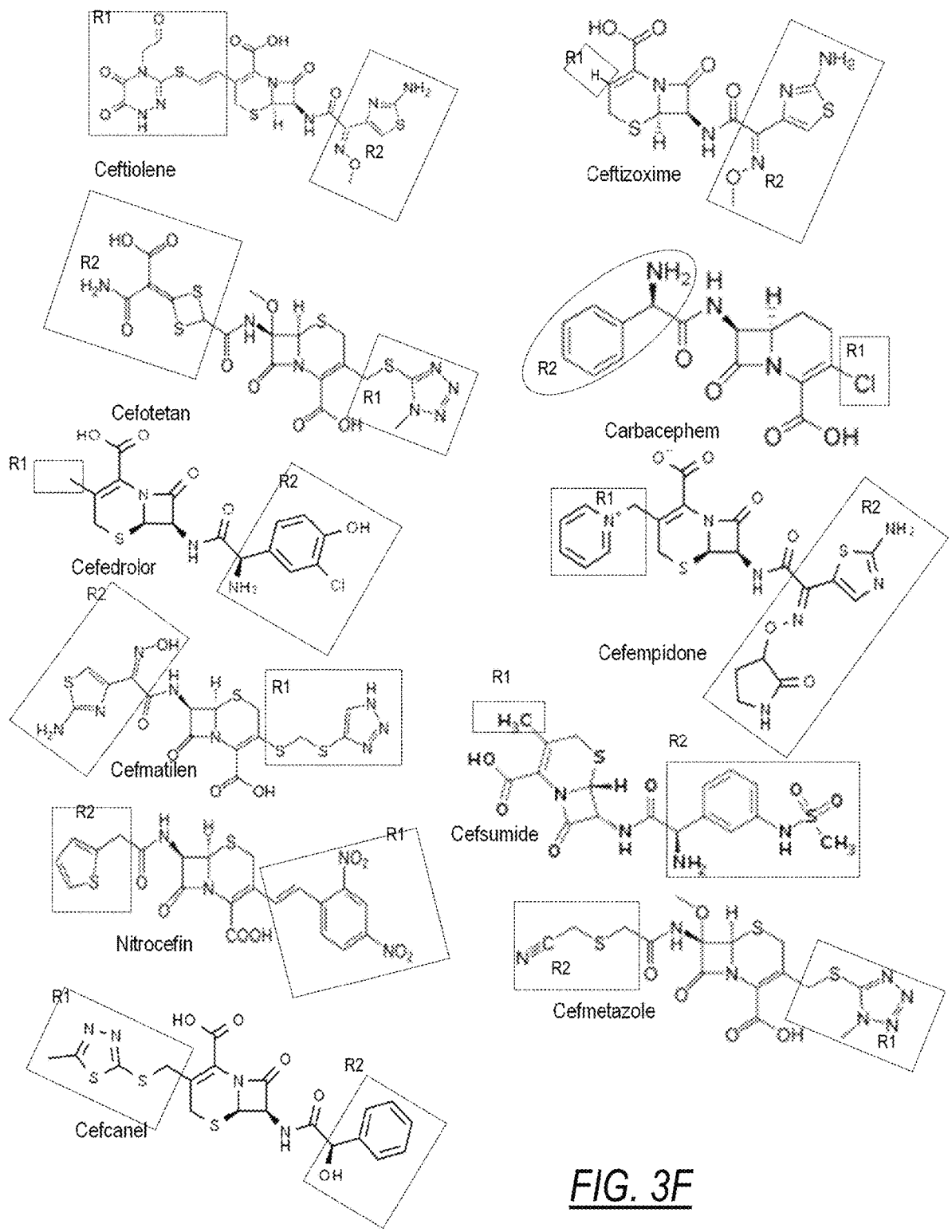
FIG. 3F shows examples of cephalosporins with examples of R1 and R2 groups indicated.

Formulas B and C in FIG. 2 illustrate two examples of Formula 1 with particular R groups identified. In Formula 2, R1 is methyl and R2 is

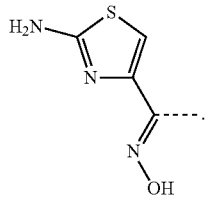

Formula 2 is an antifibrotic derivative of cefdinir. In Formula 3, R1 is methyl and R2 is

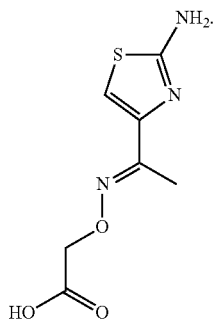

Formula 3 is an antifibrotic derivative of cefixime.

FIGS. 3A-F, which span multiple drawing sheets, provide additional examples of cephalosporins from which the compounds of Formula 1 may be derived. In each example of FIG. 3A-F, the R1 and R2 group that may be in the corresponding compound of Formula 1 is indicated.

Any of the compounds of Formula 1 or any combination thereof may be administered as an active ingredient in a pharmaceutical composition. In such a case, the compounds of Formula 1 may be blended with one or more ingredients useful for making the composition into a pharmaceutically acceptable dosage form such as a suspension, tablet, capsule, injectable, dermal patch, or other dosage form. Exemplary ingredients include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

The pharmaceutical dosage form may be substantially cephalosporin free. A dosage form may be substantially cephalosporin free, for example, it is includes 0%-5% w/w cephalosporin in the dosage form.

Certain examples of the dosage form have substantially no antibacterial efficacy as explained above. By having substantially no antibacterial efficacy, the dosage form may be safer for treating fibrotic conditions.

The dosage form may include a therapeutically effective amount of a compound of Formula 1, which is at least the minimum amount that provides the intended therapeutic effect on the patient treated, such as improving the symptoms of a fibrotic condition. In human patients, an effective amount range is often 0.1-1,000 mg/day, 0.1-25 mg/day, 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective.

In terms of effective amount by body weight, an effective amount may be about 0.001 mg/kg to about 20 mg/kg; about 5 mg/kg to about 15 mg/kg; about 1 mg/kg to about 5 mg/kg body weight; about 0.1 mg/kg to about 1 mg/kg; 0.01 mg/kg to about 0.1 mg/kg; about 0.001 mg/kg to about 0.01 mg/kg; or about 0.001 to about 0.05 mg/kg.

The pharmaceutical composition may include, for example, the following amounts of a compound of Formula 1: about 0.1 mg, about 1 mg, about 2 mg, about 2.5 mg, about 5 mg, about 10 mg, about 15 mg, about 20 mg, about 25 mg, about 30 mg, about 40 mg, about 45 mg, about 50 mg, about 60 mg, about 80 mg, about 100 mg, about 200 mg, or about 250 mg. The pharmaceutical composition may be administered once daily or multiple times daily.

These values are provided by way of example only and are not intended to limit the scope of all possible values.

The pharmaceutical composition may include a combination of different compounds of Formula 1 and may include one or more additional antifibrotic drugs or active ingredients that are therapeutically effective for treating a fibrotic condition.

The pharmaceutical composition may be administered as part of a dose regimen that includes varying changes in the dose during the treatment period.

If the pharmaceutical composition includes a solution containing a compound of Formula 1, the compound of Formula 1 concentration may be, for example, about 0.01 μM to about 1,000 μM, about 1 μM to about 500 μM, about 10 μM to about 175 μM, about 10 μM to about 150 μM, or about 10 μM to about 125 μM, or about 10 μM to about 100 μM, or about 10 μM to about 25 μM.

The effective amount may vary depending on numerous factors, including age, weight, height, severity of the disorder, administration technique, and others. The actual effective amount of a compound of Formula 1 to be administered in a given case may be determined by a physician taking into account the relevant circumstances. The amounts provided above are given as possible examples. In practice, the actual amount of a compound of Formula 1 that is administered to a patient may fall below or above these amounts, depending on the patient's needs.

One or more derivatives of the cephalosporins in FIG. 3A-F or any other cephalosporin not shown in FIG. 3A-F may be used with the proviso that the cephalosporin derivative is effective for inhibiting type 1 collagen production.

The compound of Formula 1 used in the composition described above may be a particular stereo-isomer of the compound of Formula 1. If one or more stereo-isomers of the compound of Formula 1 are determined to be more effective at inhibiting collagen production than other isomers, the % of the cephalosporin derivative administered to the patient and/or used in the pharmaceutical composition may be 50% to 100% of the more active isomer(s). In some examples, the composition may include at least 80%, at least 90%, or at least 95% of the more active isomer(s).

In some examples, it may be desirable to use a compound of Formula 1 that has reduced antibacterial efficacy or substantially no antimicrobial efficacy. This property makes the compound of Formula 1 safer for use as an antifibrotic drug.

If one or more stereo-isomers of Formula 1 are determined to be more effective at inhibiting collagen production than other isomers, the % of the compound of Formula 1 administered to the patient and/or used in the pharmaceutical composition may be 50% to 100% of the more active isomer(s). In some examples, the composition may include at least 80%, at least 90%, or at least 95% of the more active isomer(s).

A particular example of a therapeutically effective compound of Formula 1 is Formula 2 or Formula 3. Formula 3 is called CID 71314610 in the Examples section.

If one or more isomers of Formula 2 or 3 are determined to be more effective at inhibiting collagen production than other isomers, the % of the cefixime administered to the patient and/or used in the pharmaceutical composition may be 50% to 100% of the more active isomer(s). In some examples, the composition may include at least 80%, at least 90%, or at least 95% of the more active isomer(s). Isomers of Formula 2 include the following two diastereomers: CC1C2=C(C(=O)O1)NC(SC2)CNC(=O)C(=NOCC(=O)O)C3=CSC(=N3)N and CC1C2=C(C(=O)O1)N[C@H](SC2)CNC(=O)/C(=N\OCC(=O)O)/C3=CSC(=N 3)N (Isomeric Smiles).

In some examples, the compound of Formula 1 is effective to inhibit binding of LARP6 with the 5' stem-loop of collagen mRNAs, thereby inhibiting collagen synthesis.

The compound of Formula 1 used in the composition may be a pharmaceutically acceptable salt and/or derivative of a compound of Formula such as any of the examples mentioned herein so long as the pharmaceutically acceptable salt and/or derivative is effective for inhibiting type 1 collagen synthesis.

An example of a method of inhibiting type 1 collagen synthesis includes contacting at least one cell expressing type 1 collagen with a cephalosporin derivative, the cephalosporin derivative being effective for inhibiting type 1 collagen synthesis by the at least one cell.

"Contacting" may be achieved by placing the cephalosporin derivative in direct physical association with the cell(s). This is achieved using either a solid, liquid, or gaseous form of a composition containing the cephalosporin derivative. It includes events that take place both intracellularly and extracellularly and may be accomplished by any of the administration techniques set forth herein or any conventional drug administration technique.

An example of a method of treating a patient having a fibrotic condition includes administering to the patient a therapeutically effective amount of a compound of Formula 1 or the dosage form described above.

The "patient" may be a human or animal patient that has been identified as having a fibrotic condition.

Examples of fibrotic conditions include but are not limited to a pulmonary fibrosis, a liver fibrosis, a heart fibrosis, a circulatory system fibrosis, a skin fibrosis, a renal fibrosis and/or an intestinal fibrosis.

There are many different ways that the compound of Formula 1 or the composition may be administered to the patient. These administration techniques include, but are not limited to administering one or more pharmaceutically acceptable dosage forms such as suspensions, tablets, suppositories, capsules, injectables, transdermals or the like. Other suitable administration techniques include oral, sublingual, buccal, intravenous, subcutaneous, transcutaneous, intramuscular, intracutaneous, intrathecal, epidural, intraocular, intracranial, inhalation, intranasal, or the like. Any combination of administration techniques may also be used.

An oral dosage form such as a pill includes the compound of Formula 1 combined with conventional excipients for tablet, capsule, or other pill-type dosage forms. The pill dosage form may be monolithic or particulate. Typical pill excipients may include binders such as sugars, gelatin, cellulose, starch, methyl cellulose, ethyl cellulose, hydroxypropyl methyl cellulose, and the like. They may also include fillers such as lactose, sucrose, cellulose, calcium carbonate, and the like. The pill may be formulated for extended or immediate release. If needed, the pill may be enteric coated.

An injectable dosage form may include the compound Formula 1 in a liquid carrier such as saline, oil, alcohol, or the like, optionally combined with a surfactant to aid solubility or emulsification of the compound Formula 1.

EXAMPLES

This section provides an example of an antifibrotic compound that inhibits collagen production. This example is provided for illustration purposes and is not intended to limit the scope of what may be claimed.

Example 1: A Component of Commercial Cefixime Preparations Inhibits Type 1 Collagen Synthesis LARP6 regulates of type I collagen expression in fibrosis, which is characterized by excessive synthesis of type 1 collagen in various organs. LARP6 binds a unique sequence present in type 1 collagen mRNAs, which is the 5' stem-loop (5'SL). This binding regulates the translation of type 1 collagen mRNAs and is necessary for fibrosis development in vivo. Mice in which binding of LARP6 to 5'SL is genetically abolished are resistant to liver fibrosis. This indicates that the inhibitors of LARP6 binding to collagen mRNAs can be specific and effective antifibrotic drugs.

Treatment of cells with two commercially available cefixime preparations resulted in inhibition of type 1 collagen biosynthesis. This meant that a component of the cefixime samples may be an antifibrotic drug. Such antifibrotic activity may be enhanced by substantially inactivating or decreasing their anti-bacterial activity and by increasing their anti-LARP6 activity. The results below describe the activity of a component of commercial cefixime preparations as an antifibrotic drug.

Figure 4:
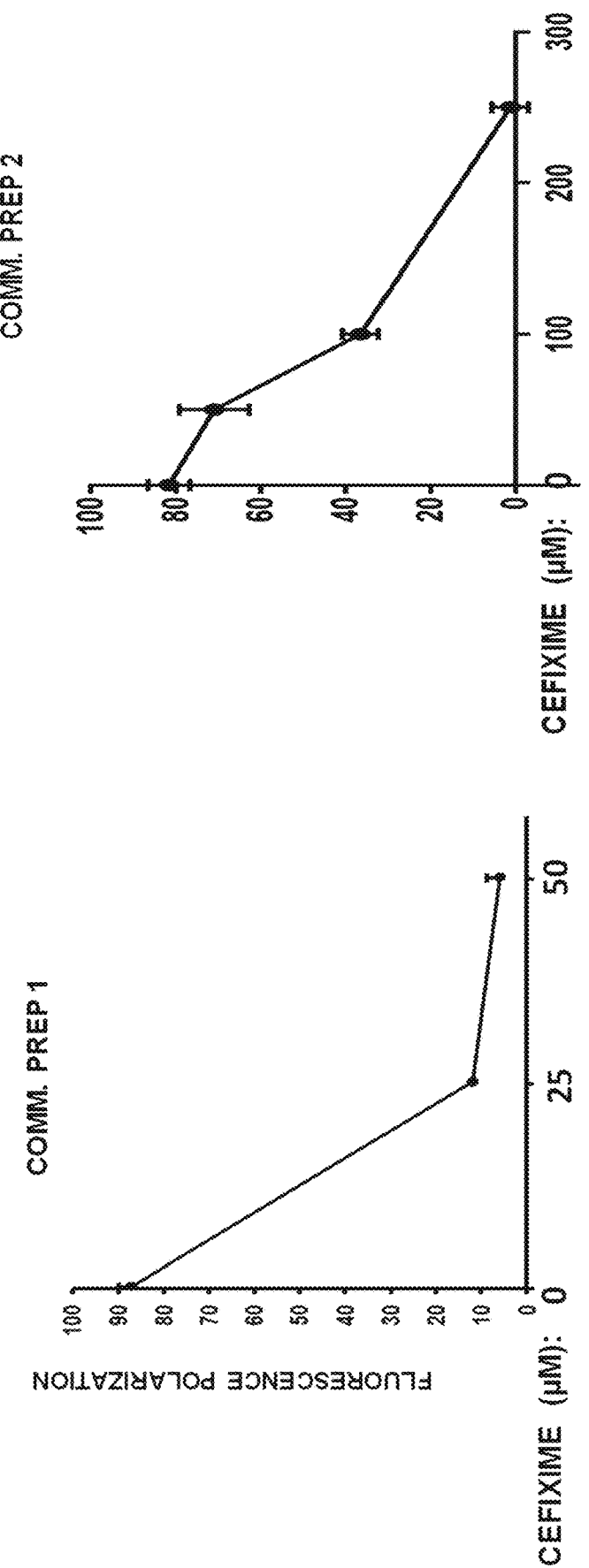
FIG. 4 is a set of graphs showing inhibition of LARP6 interaction with 5'SL of human collagen α1(I) mRNA with two different commercial preparations of cefixime.

A component of the commercial cefixime preparations inhibited the binding of LARP6 to 5'SL RNA in vitro and in vivo. FIG. 4 shows the inhibitory activity of two different commercial preparations of cefixime (comm. prep 1 and 2) on dissociation of LARP5/5'SL RNA complex in vitro. The in vitro binding of LARP6 to 5'SL RNA was monitored by measuring fluorescence polarization (FP). When pure LARP6 is bound to 5'SL RNA, FP is high and when the protein dissociates, the FP decreases. FIG. 4 shows the inhibitory potential of two cefixime preparations. Preparation 1 almost completely displaced LARP6 from 5'SL RNA at 25 µM, while preparation 2 needed 200 µM to produce a similar effect.

To compare the preparations based on their composition of stereo-isomers, the elution profile from HPLC column was used. This analysis showed that preparation 1 and preparation 2 were different. Cefixime from preparation 1 eluted from the column as multiple peaks centered around 17.2 min elution time, while cefixime from preparation 2 centered as peaks around 17.35 min elution time.

Figure 5:
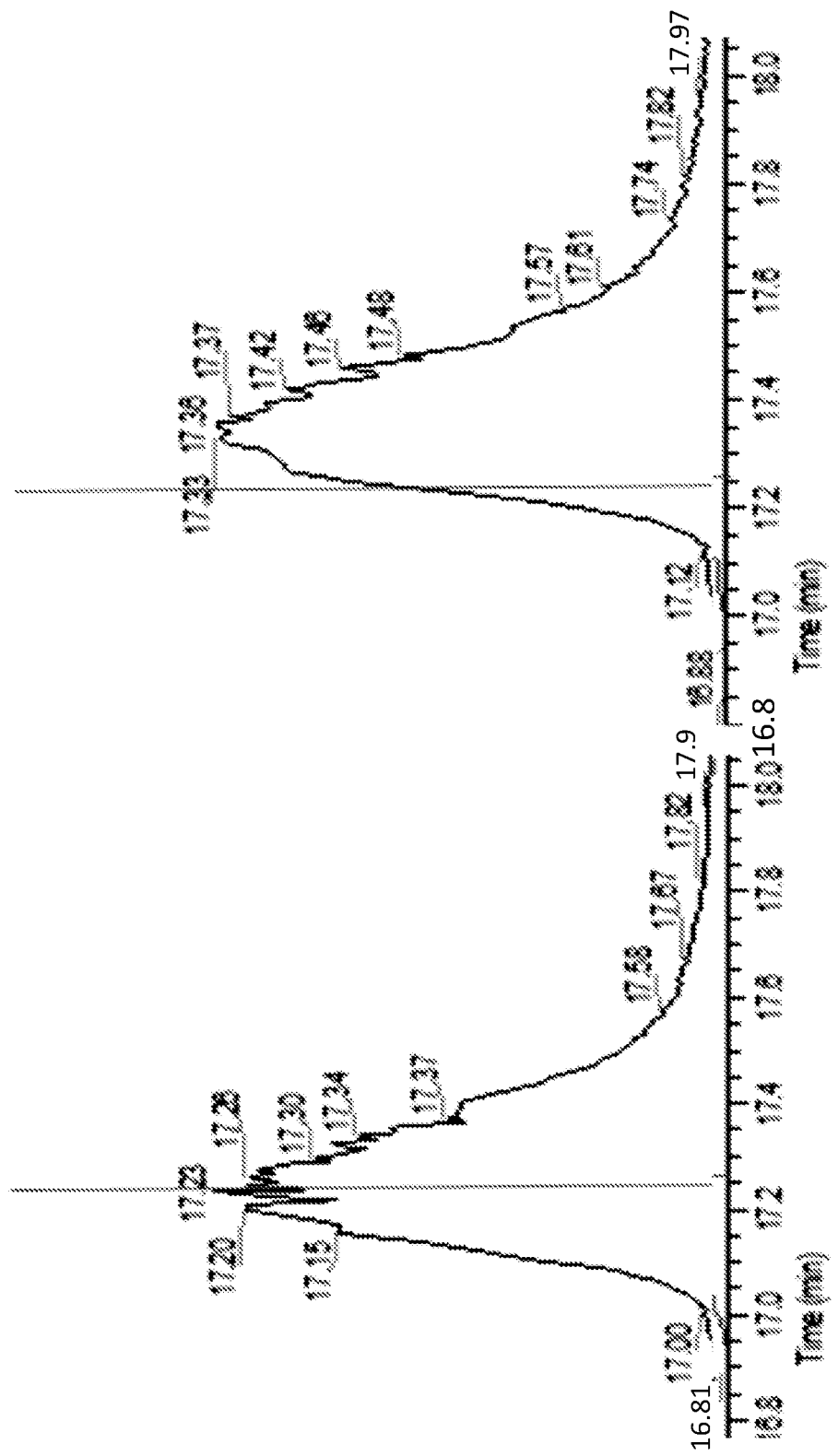
FIG. 5 is a set of graphs showing different composition of stereo-isomers in cefixime from commercial preparation 1 and commercial preparation 2 resolved by HPLC.
Figure 6:
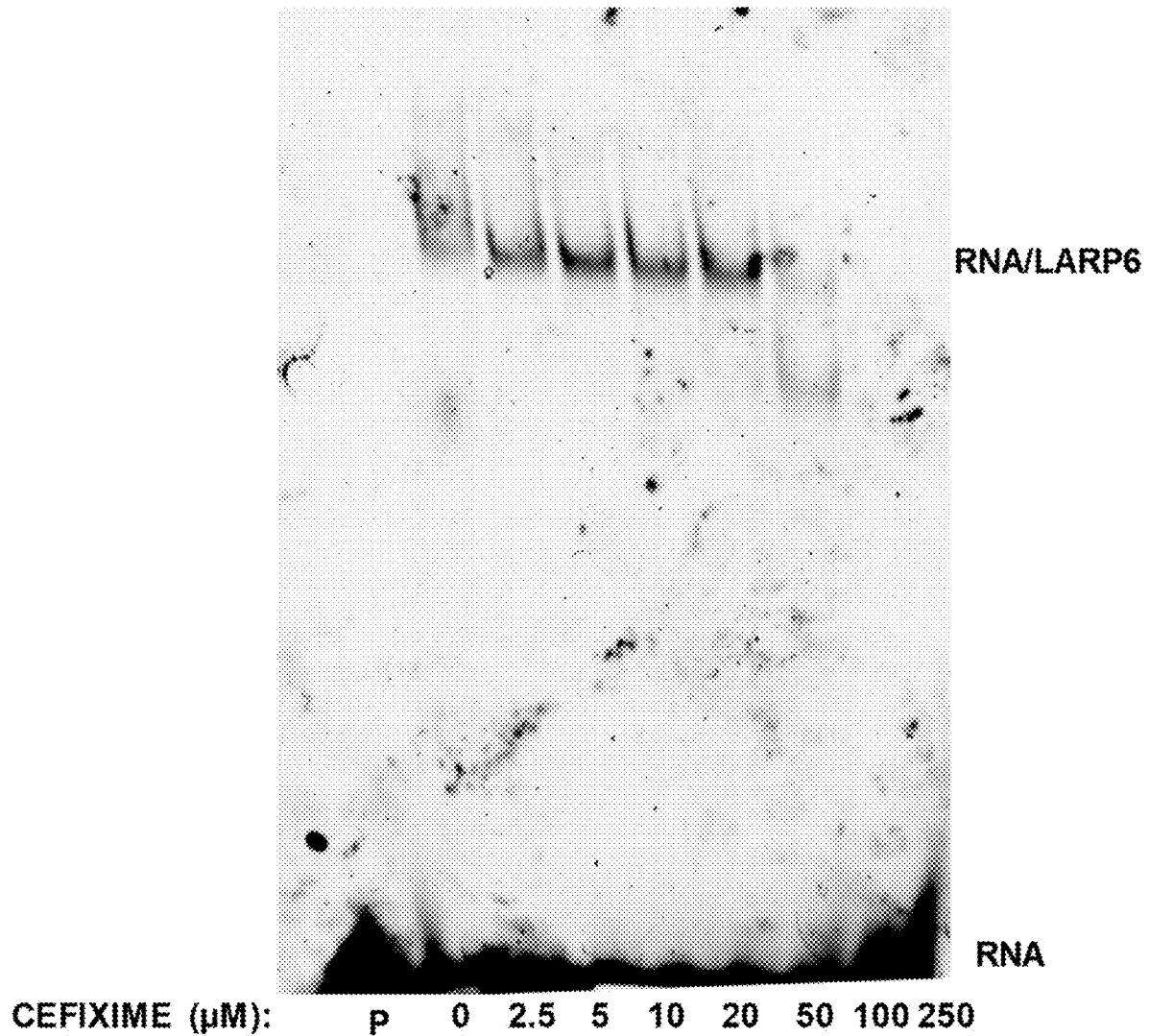
FIG. 6 is a result of a gel mobility shift experiment showing that cefixime dissociates the LARP6/5'SL RNA complex in vitro.

FIG. 5 shows the elution profiles with the vertical line indicating elution time of 17.2 min. This analysis indicated that preparation 1 and 2 contained different proportions of the stereo-isomers. Next, the inhibition of LARP6 binding was tested by gel mobility shift experiments in which binding of purified LARP6 to 5'SL RNA was resolved as protein/RNA complex in gel electrophoresis. FIG. 6 shows LARP6/5'SL RNA complexes formed in the presence of increasing concentrations of cefixime preparation 1. P is the lane showing RNA only, while lane 0 shows complex formation without cefixime. With 2.5 µM of cefixime preparation 1 there was a change in electrophoretic mobility of RNA/LARP6 complex, suggesting dissociation of some molecules, while at 50 µM the complex was almost completely dissociated. This result provided direct evidence that a component of these commercial cefixime preparations can abrogate the LARP6/5'SL RNA complex.

Figure 7:
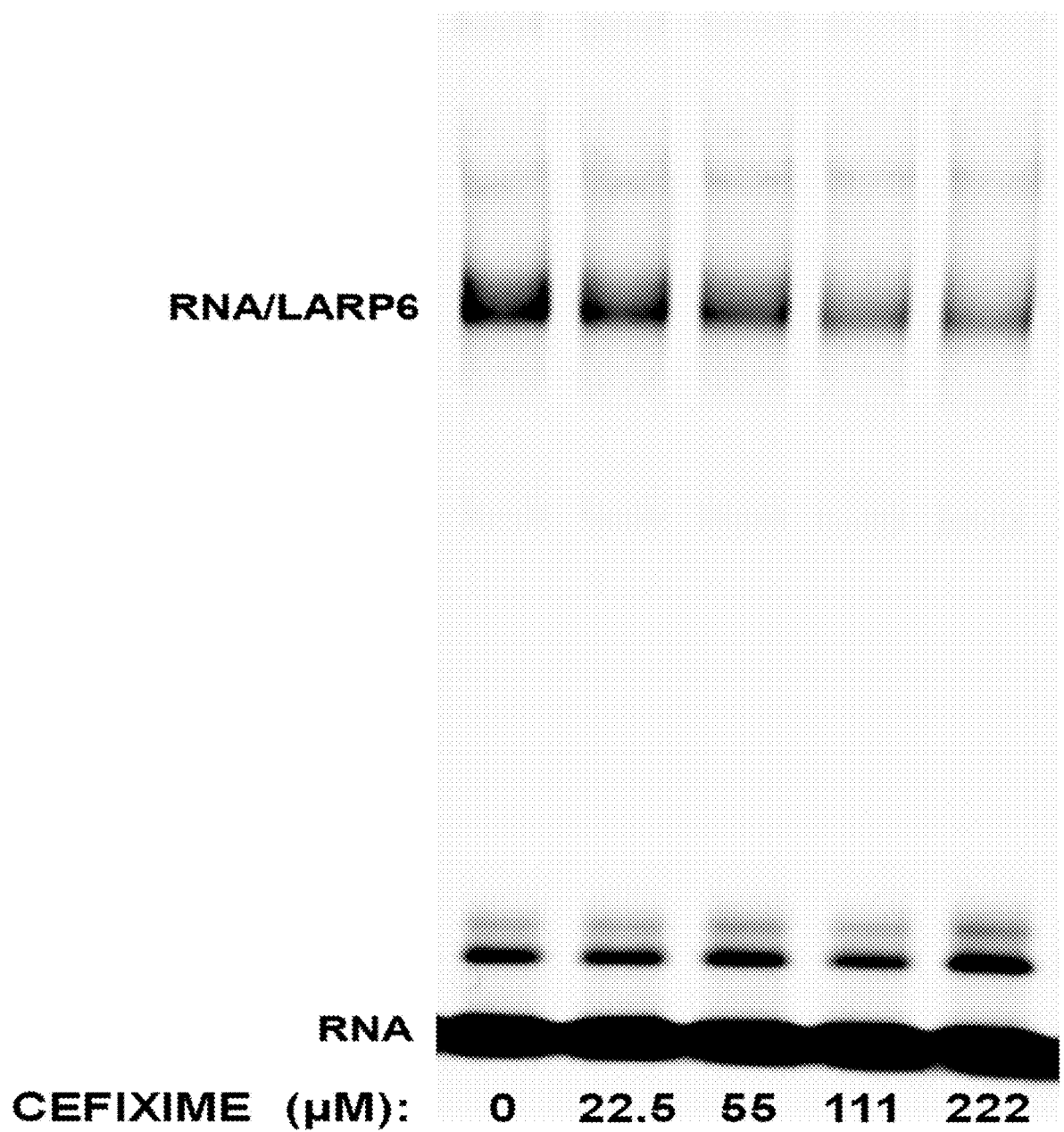
FIG. 7 is a result of a gel mobility shift experiment showing decreased binding activity of endogenous LARP6 in cell extracts treated with cefixime.

To verify that these commercial cefixime preparations can inactivate the binding activity of LARP6 in vivo, human lung fibroblasts in culture were treated with increasing concentrations of cefixime preparation 1, cellular extracts were prepared, and binding of the endogenous LARP6 in the extract to 5'SL RNA probe was assessed by gel mobility shift. FIG. 7 shows that treatment of cells with cefixime preparation 1 compromised the binding ability of endogenous LARP6 in concentration dependent manner, with the first effect seen with 22.5 µM cefixime preparation 1.

Figure 8:
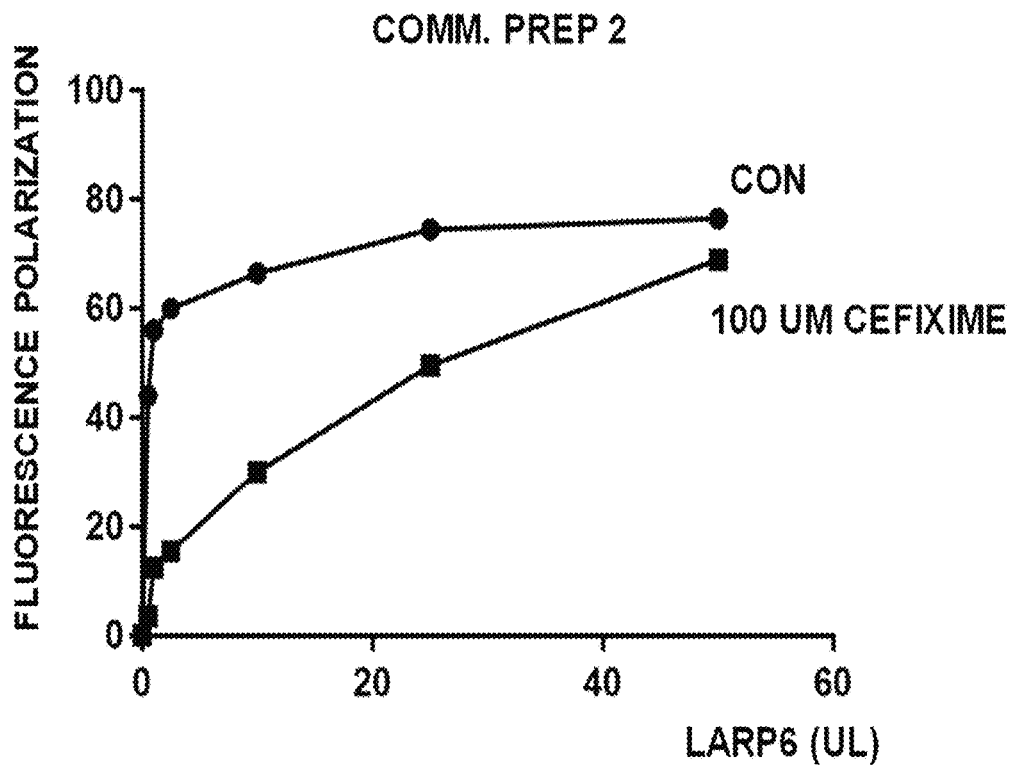
FIG. 8 is a result of a fluorescence polarization experiment showing in vitro binding affinity of LARP6 in absence or presence of cefixime.

To show that cefixime preparation 1 reduces the binding affinity of LARP6 to 5' SL the binding curves of LARP6 to 5'SL RNA in the absence and presence of cefixime preparation 1 were compared. When purified LARP6 was added in increasing amounts to a fixed amount of 5'SL RNA, typical saturation curves were obtained. FIG. 8 shows that, in absence of either commercial cefixime preparation, 50% of saturation was achieved with miniscule amounts of LARP6, while, in the presence of cefixime preparation 1, about 50-fold more LARP6 was needed to achieve the 50% saturation. This indicated that cefixime preparation 1 dramatically reduced the binding affinity of LARP6 to 5'SL RNA.

Figure 9:
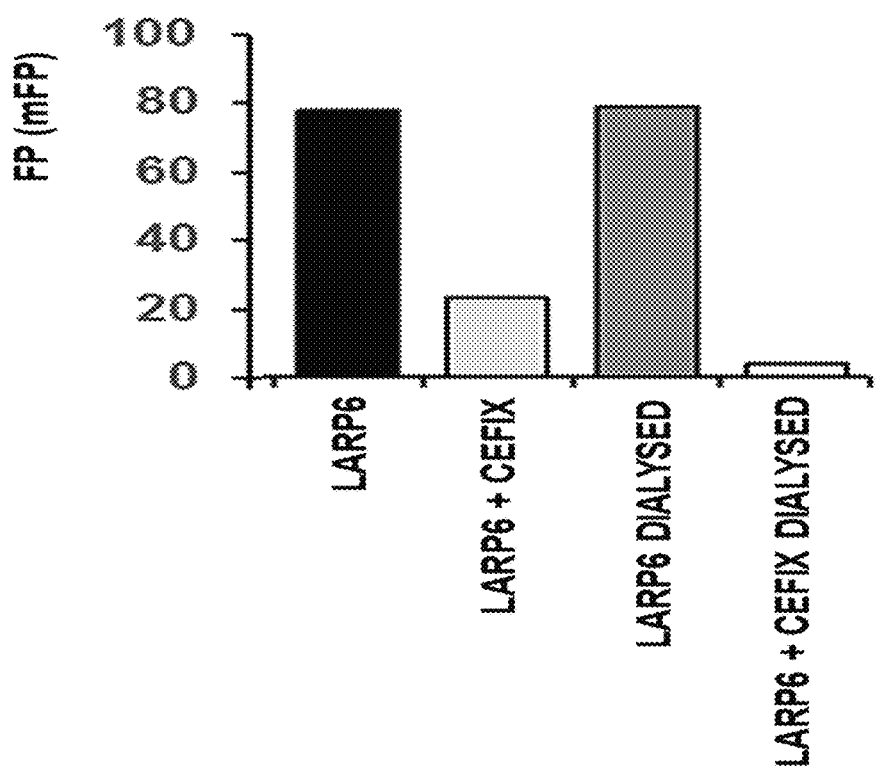
FIG. 9 is a result of a fluorescence polarization experiment showing that the interaction of cefixime with LARP6 is stable and that the drug remains bound and inactivates the ability of protein to bind 5'SL RNA after prolonged dialysis.

To assess if the reduced binding affinity of LARP6 to 5'SL RNA is caused by the attachment of a component of cefixime preparation 1 to LARP6, cefixime preparation 1 was added to purified LARP6 and incubated for 30 min to equilibrate the reaction. The protein/cefixime preparation 1 component complex was then dialyzed overnight. In the case that the cefixime preparation 1 component is not stably attached to LARP6, it will be dialyzed away and LARP6 will regain the ability to bind 5'SL RNA. FIG. 9 shows that the dialyzed LARP6/cefixime component was inactive in recognizing 5'SL RNA, suggesting that the cefixime component remained stably bound to LARP6 or that it irreversibly inactivated the protein. This provided evidence that the cefixime component interacts with LARP6 to exert its inhibitory activity.

Based on the ability of the cefixime preparation 1 component to inhibit LARP6/5'SL interaction, cefixime preparation 2 was tested to inhibit type 1 collagen production by human lung fibroblasts. The cells were treated with cefixime preparation 2 in a range of concentrations for 18 hours. The cellular medium was changed and the accumulation of type I collagen into the fresh medium was measured after 3 hours. This provided an estimate of the rate by which the cells can secrete type I collagen.

Figure 10:
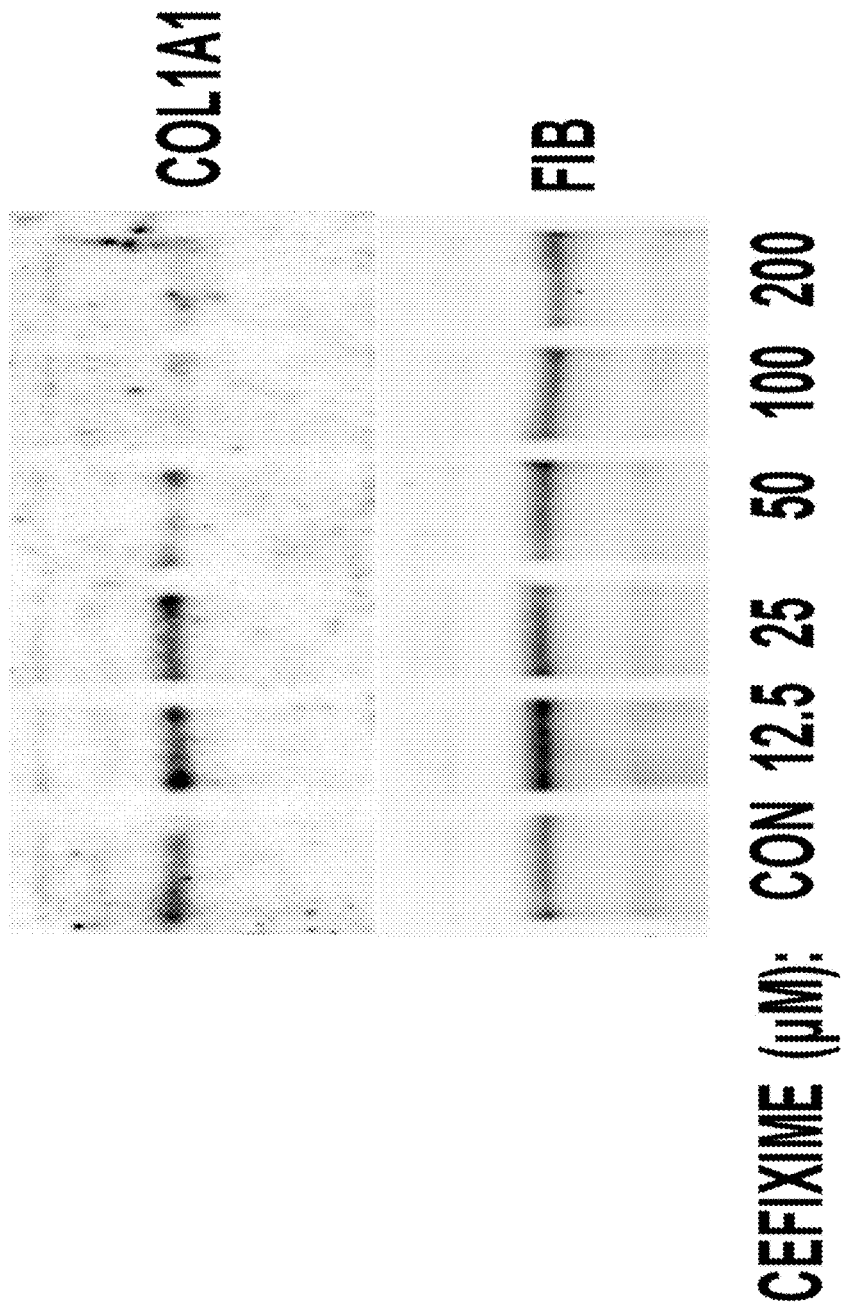
FIG. 10 is a result of a western blot experiment showing inhibition of type I collagen (COL1A1) production by lung fibroblasts treated with increasing concentrations of cefixime. FIB, fibronectin, was the loading control.

FIG. 10 shows a western blot of the collagen α1(I) polypeptide accumulated in the medium. Cefixime preparation 2 at 50 µM or at higher concentrations significantly decreased type I collagen secretion. At 50 µM, secretion of type I collagen was reduced by about 50%. At 100 µM it was reduced by about 80%. Secretion of another extracellular protein, fibronectin, was not affected, suggesting the collagen specific effect. 50 µM is the concentration of cefixime preparation 2 which is also shows the first effect in vitro. The more potent preparation 1 reduced type I collagen secretion at concentrations of 10-25 µM. This provided evidence that a component of commercial cefixime preparations can act as antifibrotic drugs.

These data prove the unexpected discovery that at least some components of commercial cephalosporin preparations have activity against LARP6 and can inhibit collagen synthesis. The evidence suggests that cefixime derivatives and other cephalosporin derivatives may stably interact with LARP6 and diminishes its binding affinity for the 5'SL. Different commercial preparations of cefixime have different activity, because they contain different proportions of the active derivative. This implicates that the anti-LARP6 activity of cefixime derivatives. The inhibitory effect of commercial preparations on type I collagen production was at 10-50 µM. This concentration can be dramatically lowered if the active derivative is used rather than the commercial cefixime preparation.

Example 2: Identification of CID 71314610 as the Active Compound

Figure 11:
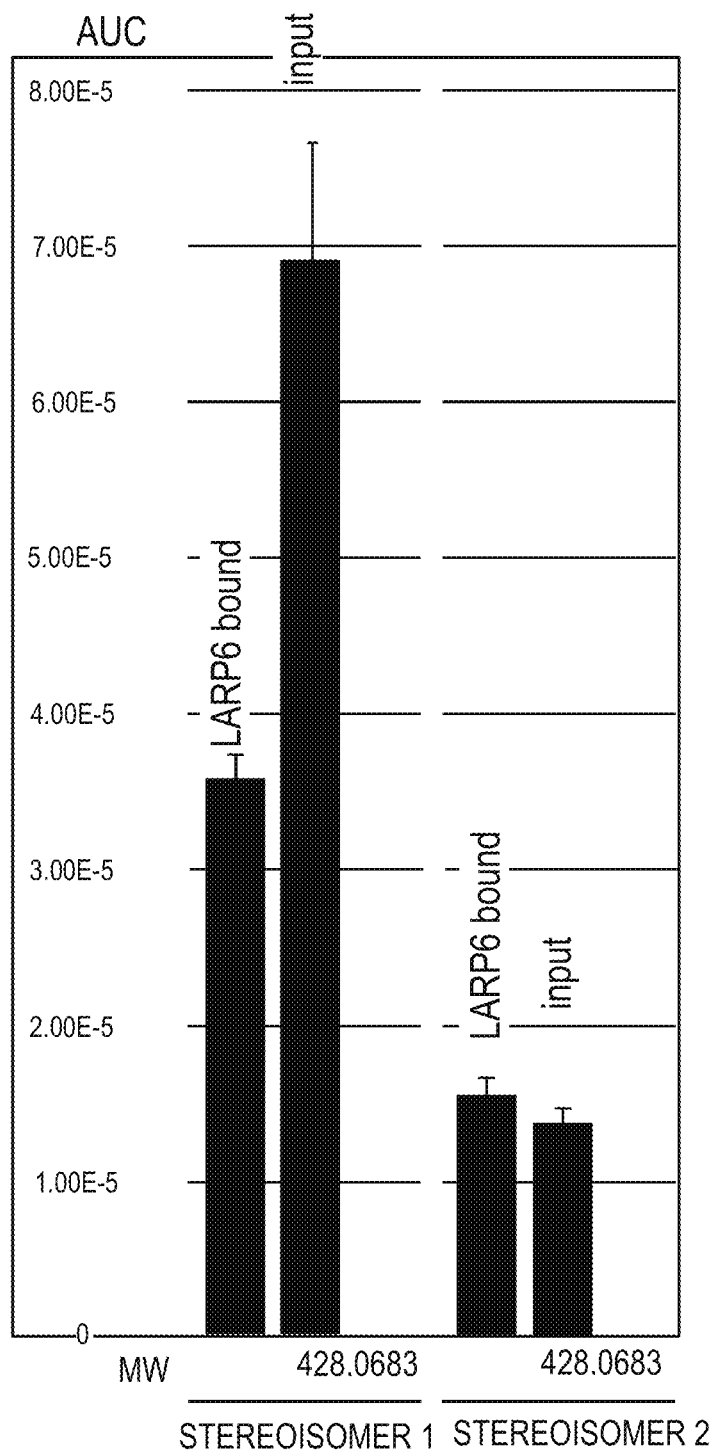
FIG. 11 is a bar graph of showing the identification of CID 71314610 as the component of commercial cefixime preparations, which binds LARP6. Input: amount of CID 71314610 present in the original cefixime preparation. LARP6 bound: the fraction sequestered by LARP6.

The component with antifibrotic activity in the commercial cefixime preparations was identified by affinity binding of the commercial cefixime preparations to the purified LARP6 protein, followed by elution of the bound molecular species and their identification by mass spectrometry. FIG. 11 shows that a component with molecular weight of 428.0683 was preferentially bound to LARP6 (Cefixime itself has molecular weight of 453.5). This component has two diastereomer isoforms which were present in miniscule amounts in the commercial cefixime preparations, but both were sequestered by LARP6 protein.

CID 71314610 has the chemical name: 2-[[[(Z)-1-(2-Aminothiazol-4-yl)-2-[[[(2R,5RS)-5-methyl-7-oxo-1,2,5,7-tetrahydro-4H-furo[3,4-d][1,3]thiazin-2-yl]methyl]amino]-2-oxoethylidene] amino]oxy]acetic acid. InChI=1S/C15H17N5O6S2/c1-6-7-4-27-9(19-11(7)14(24)26-6)2-17-13(23)12(20-25-3-10(21)22)8-5-28-15(16)18-8/h5-6,9,19H,2-4H2,1H3,(H2,16,18)(H,17,23)(H,21,22)/b20-12-/t6?,9-/rnn1/s1. Molecular Formula C15H17N5O6S2. molecular weight 427.5. CAS 1335475-19-8. It is also known as Cefixime impurity B.

FIG. 11 shows that 50% of one diastereomer and 100% of the other diastereomer that were present in the input Cefixime preparation were bound by LARP6.

The structure of CID 71314610 does not contain the lactam ring, which is needed for antimicrobial activity of cefixime, but it retains the imine side group useful for oral bioavailability.

CID 71314610 binds LARP6 protein as shown in FIG. 11. By interacting with LARP6, it inhibits LARP6 ability to bind 5' stem-loop of collagen mRNAs and this suppresses type I collagen production by profibrotic cells.

Figure 12:
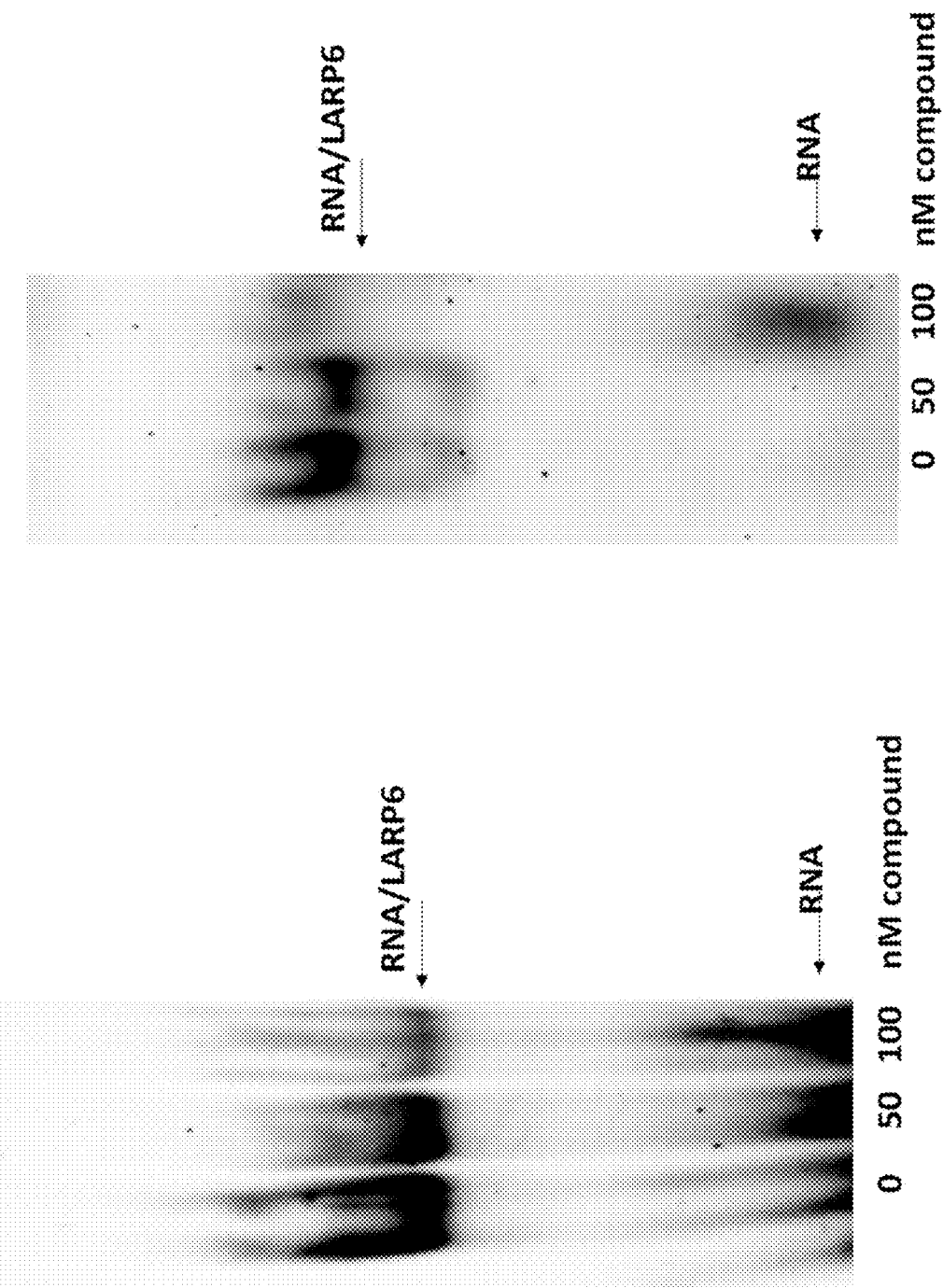
FIG. 12 is gel mobility shift data showing the effect of the CID 71314610 on LARP6 binding to 5' stem-loop RNA in vitro.

To assess the efficacy of CID 71314610 in inhibiting LARP6 binding to its target sequence, the 5' stem-loop of type I collagen mRNAs, recombinant LARP6 protein was added to 5' stem-loop RNA in vitro and CID 71314610 was added at nano-M concentrations to the reaction. The formation of LARP6/RNA complex was analyzed by electrophoretic mobility shift assay. FIG. 12 shows two independent experiments. Dissociation of 50% of LARP6/RNA complexes was seen at 50 nM of CID 71314610 and ~90% of LARP6 was dissociated at 100 nM.

Figure 13:
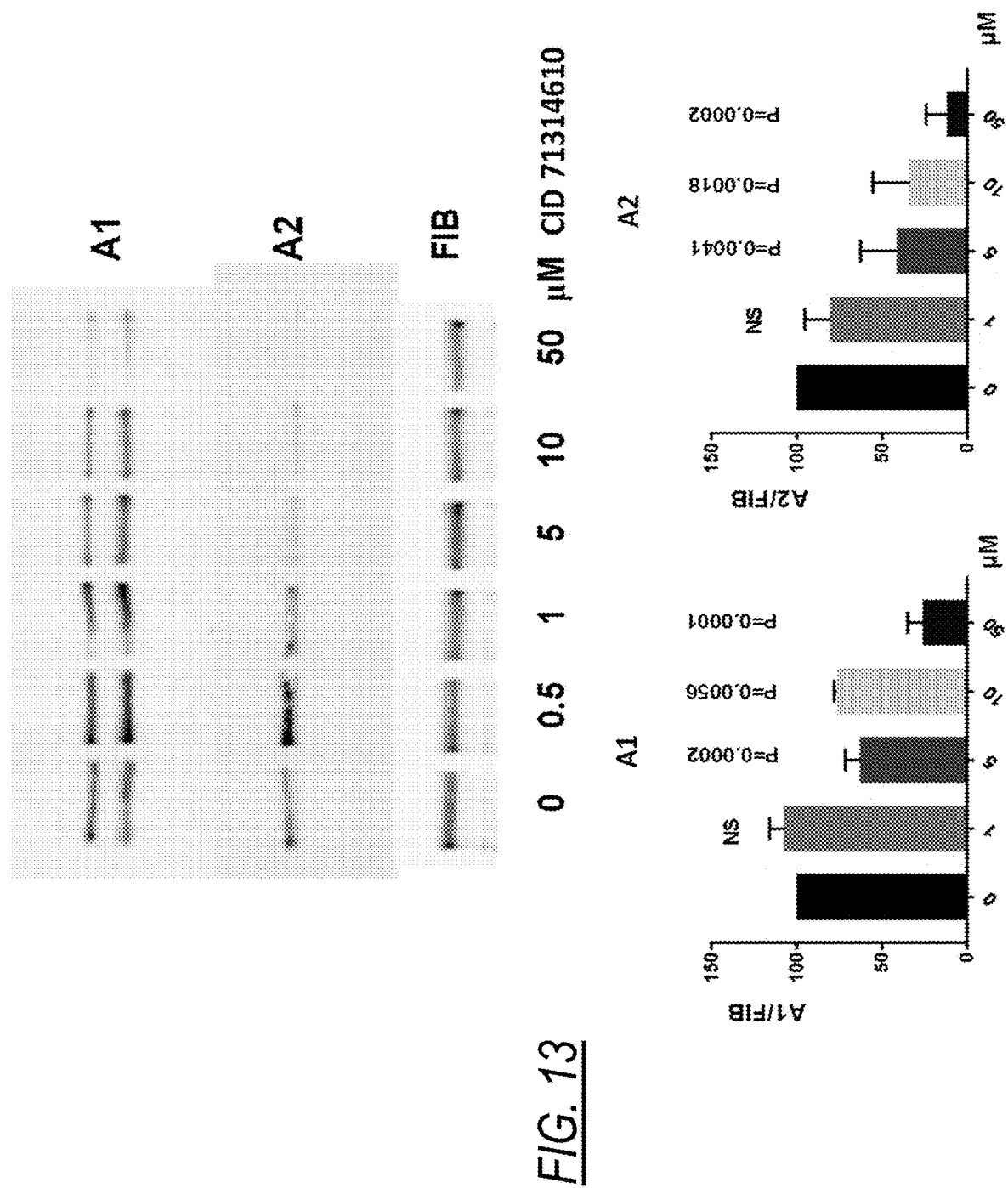
FIG. 13 is data showing the inhibition of type I collagen production by human lung fibroblasts. The upper panel is a representative Western blot.

Human lung fibroblasts are responsible for lung fibrosis. These cells were cultured in vitro and CID 71314610 was added to the cellular medium at 0.5-50 μM. After overnight incubation the medium was changed and secretion of type I collagen into the fresh medium was analyzed by western blot. The rate of collagen secretion into the medium is a measure of the profibrotic activity of cells. Type I collagen is composed of two polypeptides, α1(I) and α2(I), so both were analyzed. FIG. 13, upper panel, shows a representative experiment. The secretion of α1(I) (A1) and α2(I) (A2) collagen polypeptides was inhibited by CID 71314610 in the concentration dependent manner. The secretion of fibronectin (FIB) was not affected by CID 71314610, suggesting that CID 71314610 specifically inhibits type I collagen production. In three independent experiments the expression of α1(I) and α2(I) polypeptides was normalized to the expression of fibronectin and plotted as function of CID 71314610 concentration (FIG. 13, bottom panel). Highly statistically significant inhibition of both polypeptides comprising type I collagen was seen at 5 μM of CID 71314610.

This demonstrated that CID 71314610 has potent antifibrotic activity on human lung fibroblasts and, very likely, also on other types of collagen producing cells.

Fibrosis is a chronic disease that requires years of therapy, so antifibrotic drugs should be specific for type I collagen, substantially nontoxic and orally bioavailable. Cefixime is one of the least toxic drugs, so it is likely that CID 71314610 is also nontoxic. CID 71314610 does not have the original antimicrobial activity, so may be used safely. Its pharmacokinetics may also be similar to that of Cefixime. Cefixime is orally bioavailable and CID 71314610 retains the chemical structure conferring the oral bioavailability. CID 71314610 targets LARP6, which is the specific regulator of type I collagen expression, therefore, CID 71314610 represents specific antifibrotic drug. Based on these facts, this invention is to repurpose CID 71314610 for treatment of fibrosis of various organs.

The chemical structures provided herein are intended to generally illustrate the structure of the molecule and are not intended to be limited thereto. Instead, the structures are provided to show where the general constituents are located on each molecule. For example, the structures are not intended to be limited to the particular stereoisomer shown. The compounds should be understood to include all of the stereoisomers that occur with a given structure.

This disclosure describes example embodiments, but not all possible embodiments of the compositions and methods. Where a particular feature is disclosed in the context of a particular embodiment, that feature can also be used, to the extent possible, in combination with and/or in the context of other embodiments. The methods and compositions may be embodied in many different forms and should not be construed as limited to only the embodiments described here.

What is claimed is:

1. A composition comprising a pharmaceutical dosage form that is substantially cephalosporin free and includes an antifibrotic compound of formula

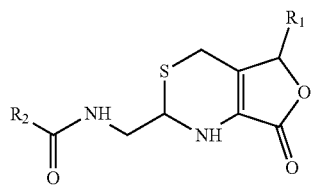

wherein where $R_1$ includes at least one member selected from the group consisting of H, alkyl, alkenyl, alkynyl, aryl, hydroxy, carboxy, acyl, nitro, phosphor, halo, sulfo, ester, ether, and amino; $R_2$ is selected from

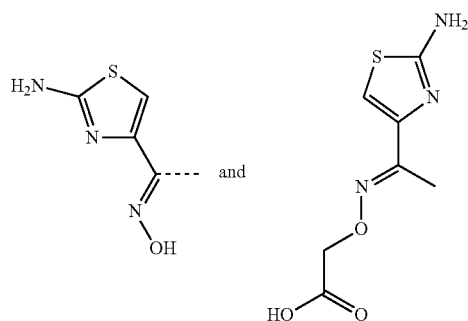

or a pharmaceutically acceptable salt thereof and wherein the pharmaceutical dosage form has no substantial antibacterial efficacy.

2. The composition of claim 1, wherein substantially cephalosporin free is 0%-5% w/w cephalosporin in the pharmaceutical dosage form.

3. The composition of claim 1, wherein the formula is

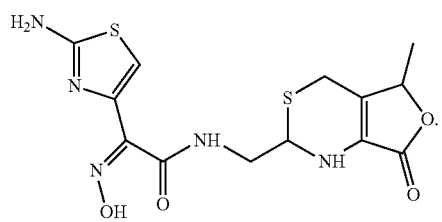 [SMILES: CC1OC(=O)C2=C1CSC(CNC(=O)/C(=N\O)c1csc(N)n1)N2]

4. The composition of claim 1, wherein the formula is

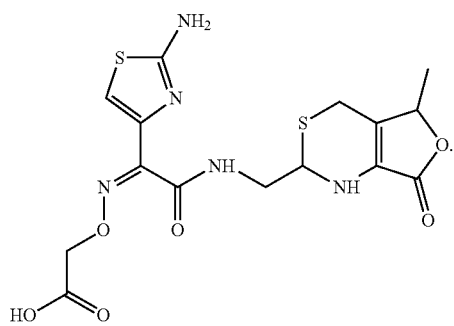 [SMILES: CC1OC(=O)C2=C1CSC(CNC(=O)/C(=N\OCC(=O)O)c1csc(N)n1)N2]

5. A method comprising administering to a patient having a fibrotic condition a therapeutically effective amount of the composition of claim 1 to the patient.

6. The method of claim 5, wherein substantially cephalosporin free is 0%-5% w/w cephalosporin in the pharmaceutical dosage form.

7. The method of claim 5, wherein the formula is

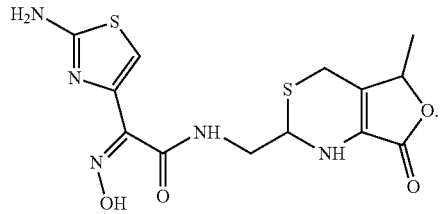 [SMILES: CC1OC(=O)C2=C1CSC(CNC(=O)/C(=N\O)c1csc(N)n1)N2]

8. The method of claim 5, wherein the formula is

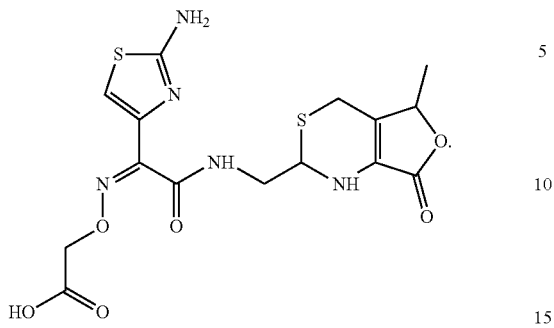

9. The method of claim 5, wherein the fibrotic condition is at least one of a pulmonary fibrosis, a liver fibrosis, a heart fibrosis, a brain fibrosis, a circulatory system fibrosis, a skin fibrosis, and an intestinal fibrosis.

10. The method of claim 5, wherein administering is oral administration and/or administration by injection.

* * * * *